(12) United States Patent
Chavan et al.

(10) Patent No.: US 12,741,075 B2
(45) Date of Patent: Sep. 22, 2026

(54) VACUUM CHAMBER WITH SNAP FIT PLUNGER MECHANISM

(71) Applicant: C. R. Bard, Inc., Franklin Lakes, NJ (US)

(72) Inventors: Varad Chavan, Kolhapur (IN); Rohit Sinha, Lawrenceville, GA (US); David M. Simiele, Roswell, GA (US)

(73) Assignee: C. R. Bard, Inc., Franklin Lakes, NJ (US)

(*) Notice: Subject to any disclaimer, the term of this patent is extended or adjusted under 35 U.S.C. 154(b) by 986 days.

(21) Appl. No.: 17/701,395

(22) Filed: Mar. 22, 2022

(65) Prior Publication Data

US 2022/0305189 A1 Sep. 29, 2022

Related U.S. Application Data

(60) Provisional application No. 63/164,951, filed on Mar. 23, 2021.

(51) Int. Cl.
*A61M 1/00* (2006.01)
*A61M 39/22* (2006.01)

(52) U.S. Cl.
CPC ................ *A61M 1/71* (2021.05); *A61M 1/67* (2021.05); *A61M 1/84* (2021.05); *A61M 39/22* (2013.01); *A61M 2039/229* (2013.01)

(58) Field of Classification Search
CPC ............ A61M 1/71; A61M 1/67; A61M 1/84; A61M 39/22; A61M 2039/229
(Continued)

(56) References Cited

U.S. PATENT DOCUMENTS 3,114,916 A 12/1963 Hadley
3,583,401 A 6/1971 Vailiancourt et al.
(Continued)

FOREIGN PATENT DOCUMENTS

CN 106955208 A 7/2017
CN 116650740 A 8/2023
(Continued)

OTHER PUBLICATIONS

U.S. Appl. No. 17/542,060, filed Dec. 3, 2021 Non-Final Office Action dated Jun. 27, 2023.
(Continued)

*Primary Examiner* — Andrew J Mensh
(74) *Attorney, Agent, or Firm* — Rutan & Tucker LLP

(57) ABSTRACT

A drainage system includes a vacuum chamber to receive drainage liquid from a drainage tube. The chamber can include an input port coupled with the drainage tube and a drain port coupled with a collection container. The system can include an air pump having an input coupled with a vacuum port of the vacuum chamber and a distal end of the drainage tube. Activation of the air pump can establish circulating fluid flow between the drainage tube and the vacuum chamber, and deactivation of the air pump can permit drainage liquid to drain from the vacuum chamber into the output tube. Also disclosed is a method of draining liquid from a patient, including accumulating a volume of the drainage liquid at a first location along a drainage pathway, moving the volume to a second location, accumulating the volume at the second location, and moving the volume to a collection container.

23 Claims, 4 Drawing Sheets

(58) Field of Classification Search
USPC .......................................................... 604/320
See application file for complete search history.

(56) References Cited

U.S. PATENT DOCUMENTS 3,598,124 A 8/1971 Andersen et al.
3,661,143 A 5/1972 Henkin
3,707,972 A 1/1973 Villari et al.
3,861,394 A 1/1975 Villari
3,901,235 A 8/1975 Patel et al.
3,955,574 A 5/1976 Rubinstein
4,013,076 A 3/1977 Puderbaugh et al.
4,084,593 A 4/1978 Jarund
4,250,872 A 2/1981 Tamari
4,265,243 A 5/1981 Taylor
4,266,689 A 5/1981 Asher
4,305,403 A 12/1981 Dunn
4,315,506 A 2/1982 Kayser et al.
4,360,933 A 11/1982 Kimura et al.
4,465,485 A 8/1984 Kashmer et al.
4,490,144 A 12/1984 Steigerwald
4,531,939 A 7/1985 Zumi
4,556,997 A 12/1985 Takamiya et al.
4,631,061 A 12/1986 Martin
4,654,029 A 3/1987 D'Antonio
4,711,365 A 12/1987 Fomby
4,747,166 A 5/1988 Kuntz
4,810,242 A 3/1989 Sundblom et al.
4,819,684 A 4/1989 Zaugg et al.
4,872,579 A 10/1989 Palmer
4,880,411 A 11/1989 Fangrow, Jr. et al.
4,990,137 A 2/1991 Graham
5,002,528 A 3/1991 Palestrant
5,071,411 A 12/1991 Hillstead
5,100,376 A 3/1992 Blake, III
5,186,431 A 2/1993 Tamari
5,242,404 A 9/1993 Conley et al.
5,318,550 A 6/1994 Cermak et al.
5,359,233 A 10/1994 Mumper et al.
5,405,319 A 4/1995 Abell et al.
RE35,707 E 12/1997 Takamiya et al.
5,738,656 A 4/1998 Wagner et al.
5,813,842 A 9/1998 Tamari
5,894,608 A 4/1999 Birbara
6,007,521 A 12/1999 Bidwell et al.
6,106,506 A 8/2000 Abell et al.
6,183,454 B1 2/2001 Levine et al.
7,833,186 B1 11/2010 Batiste
8,266,741 B2 9/2012 Penninger et al.
8,337,475 B2 12/2012 Christensen et al.
8,366,692 B2 * 2/2013 Weston .................. A61M 1/96 604/323
8,475,419 B2 7/2013 Eckermann
8,512,301 B2 8/2013 Ma
9,814,866 B1 11/2017 Goswami
10,363,184 B2 7/2019 Zerhusen et al.
10,391,275 B2 8/2019 Burnett et al.
10,426,919 B2 10/2019 Erbey, II et al.
10,506,965 B2 12/2019 Cooper et al.
10,737,057 B1 8/2020 Mikhail et al.
10,772,998 B2 9/2020 Luxon et al.
12,097,150 B2 9/2024 Chancy et al.
2002/0000253 A1 1/2002 Fillmore et al.
2002/0087131 A1 7/2002 Wolff et al.
2002/0161317 A1 10/2002 Risk et al.
2003/0078638 A1 4/2003 Voorhees et al.
2004/0176746 A1 9/2004 Forral
2004/0230181 A1 11/2004 Cawood
2004/0236292 A1 11/2004 Tazoe et al.
2004/0254547 A1 12/2004 Okabe et al.
2005/0183780 A1 8/2005 Michaels et al.
2005/0197647 A1 * 9/2005 Dolliver ................. A61M 1/84 604/541
2005/0209585 A1 9/2005 Nord et al.
2005/0245898 A1 11/2005 Wright et al.
2005/0256460 A1 11/2005 Rome et al.
2005/0261619 A1 11/2005 Gay
2006/0015190 A1 1/2006 Robertson
2006/0079854 A1 4/2006 Kay et al.
2006/0155260 A1 7/2006 Blott et al.
2006/0213527 A1 9/2006 Argenta et al.
2006/0235353 A1 10/2006 Gelfand et al.
2006/0270971 A1 11/2006 Gelfand et al.
2006/0271019 A1 11/2006 Stoller et al.
2007/0005002 A1 1/2007 Millman et al.
2007/0078444 A1 4/2007 Larsson
2007/0142729 A1 6/2007 Pfeiffer et al.
2007/0272311 A1 11/2007 Trocki et al.
2008/0051708 A1 2/2008 Kumar et al.
2008/0156092 A1 7/2008 Boiarski
2008/0281254 A1 11/2008 Humayun et al.
2008/0312550 A1 12/2008 Nishtala et al.
2009/0076469 A1 3/2009 Alexandersen
2009/0157016 A1 6/2009 Adahan
2009/0157040 A1 6/2009 Jacobson et al.
2009/0326483 A1 12/2009 Green
2010/0042059 A1 2/2010 Pratt et al.
2010/0106116 A1 4/2010 Simmons et al.
2010/0130949 A1 5/2010 Garcia
2010/0280435 A1 11/2010 Raney et al.
2010/0298792 A1 * 11/2010 Weston .................. A61M 1/96 604/319
2011/0060300 A1 * 3/2011 Weig ...................... A61F 5/451 604/319
2012/0036638 A1 2/2012 Penninger et al.
2012/0323144 A1 12/2012 Coston et al.
2013/0218106 A1 * 8/2013 Coston ................... A61M 1/83 604/317
2014/0053841 A1 2/2014 Ratner
2014/0200558 A1 7/2014 McDaniel
2014/0200588 A1 7/2014 Anderson et al.
2014/0276497 A1 9/2014 Robinson et al.
2015/0126975 A1 5/2015 Wuthier
2015/0141957 A1 5/2015 Hauswald
2015/0290448 A1 10/2015 Pavlik
2016/0135982 A1 5/2016 Garcia
2016/0183819 A1 6/2016 Burnett et al.
2016/0310711 A1 10/2016 Luxon et al.
2017/0014560 A1 * 1/2017 Minskoff ......... A61B 5/150099
2017/0014617 A1 1/2017 Huici
2017/0072125 A1 3/2017 Wallenås et al.
2017/0136209 A1 * 5/2017 Burnett .................. A61M 1/60
2017/0143566 A1 5/2017 Elku et al.
2017/0209630 A1 7/2017 Klusmann et al.
2017/0241978 A1 8/2017 Duval
2017/0312114 A1 11/2017 Glithero
2018/0015251 A1 1/2018 Lampotang et al.
2018/0071441 A1 3/2018 Croteau et al.
2018/0104391 A1 4/2018 Luxon et al.
2018/0110456 A1 4/2018 Cooper et al.
2018/0125697 A1 5/2018 Ferrera
2018/0177458 A1 6/2018 Burnett et al.
2018/0185222 A1 7/2018 Zerhusen et al.
2018/0235523 A1 8/2018 Sauder
2018/0245699 A1 8/2018 Lee
2018/0360424 A1 12/2018 Yurek et al.
2019/0009021 A1 1/2019 Nelson et al.
2019/0009023 A1 1/2019 Diperna et al.
2019/0030264 A1 1/2019 Herskovic et al.
2019/0038451 A1 2/2019 Harvie
2019/0046102 A1 2/2019 Kushnir et al.
2019/0126006 A1 5/2019 Rehm et al.
2019/0143008 A1 5/2019 Brundage et al.
2019/0143094 A1 5/2019 DeMeritt
2019/0151610 A1 5/2019 Fletter
2019/0175801 A1 6/2019 Levine
2019/0255242 A1 8/2019 Cull
2019/0343445 A1 11/2019 Burnett et al.
2020/0000979 A1 1/2020 Myers
2020/0061281 A1 2/2020 Desouza et al.
2020/0155751 A1 5/2020 Batiste
2020/0315837 A1 10/2020 Radl et al.
2021/0077007 A1 3/2021 Jouret et al.
2022/0152345 A1 5/2022 Simiele et al.

(56) References Cited

U.S. PATENT DOCUMENTS

| | | | |
|---|---|---|---|
| 2022/0160949 | A1 | 5/2022 | Simiele et al. |
| 2022/0176031 | A1 | 6/2022 | Cheng et al. |
| 2022/0193366 | A1 | 6/2022 | Cheng et al. |
| 2022/0218890 | A1 | 7/2022 | Chavan |
| 2022/0218973 | A1 | 7/2022 | Chavan et al. |
| 2022/0218974 | A1 | 7/2022 | Chavan et al. |
| 2022/0273213 | A1 | 9/2022 | Sokolov et al. |
| 2022/0287689 | A1 | 9/2022 | Johannes |
| 2022/0330867 | A1 | 10/2022 | Conley et al. |
| 2022/0362080 | A1 | 11/2022 | McCorquodale et al. |
| 2022/0409421 | A1 * | 12/2022 | Hughett ................ A61F 5/4408 |
| 2023/0013353 | A1 | 1/2023 | Chavan et al. |
| 2023/0030637 | A1 | 2/2023 | Gloeckner et al. |
| 2023/0054937 | A1 | 2/2023 | Chancy et al. |
| 2023/0083906 | A1 | 3/2023 | Jones et al. |
| 2023/0277199 | A1 | 9/2023 | Duffy |
| 2023/0310837 | A1 | 10/2023 | Gamsizlar et al. |
| 2024/0033404 | A1 | 2/2024 | Ishikawa |
| 2024/0238500 | A1 | 7/2024 | Simiele et al. |
| 2024/0307604 | A1 | 9/2024 | Chavan |
| 2025/0009578 | A1 | 1/2025 | Chancy et al. |
| 2025/0018147 | A1 | 1/2025 | Rehm |
| 2025/0018149 | A1 | 1/2025 | Cheng et al. |
| 2025/0025617 | A1 | 1/2025 | Chavan et al. |
| 2025/0025620 | A1 | 1/2025 | Cheng et al. |
| 2025/0040848 | A1 | 2/2025 | Lai et al. |
| 2025/0177632 | A1 | 6/2025 | Jones et al. |
| 2025/0186735 | A1 | 6/2025 | Rehm et al. |
| 2025/0288775 | A1 | 9/2025 | Simiele et al. |
| 2026/0014310 | A1 | 1/2026 | Chavan |
| 2026/0108376 | A1 | 4/2026 | Chavan et al. |

FOREIGN PATENT DOCUMENTS

| | | | |
|---|---|---|---|
| EP | 1122435 | A1 | 8/2001 |
| EP | 1872752 | A1 | 1/2008 |
| EP | 2417955 | A2 | 2/2012 |
| EP | 2730299 | A1 | 5/2014 |
| EP | 4096611 | B1 | 5/2025 |
| EP | 4585150 | A2 | 7/2025 |
| GB | 1408821 | A | 10/1975 |
| GB | 2235256 | | 2/1991 |
| WO | 2009/026237 | A1 | 2/2009 |
| WO | 2012016179 | A1 | 2/2012 |
| WO | 2015019056 | A1 | 2/2015 |
| WO | 2015/105916 | A1 | 7/2015 |
| WO | 2016012494 | A1 | 1/2016 |
| WO | 2017177068 | A1 | 10/2017 |
| WO | 2018136306 | A1 | 7/2018 |
| WO | 2018191193 | A1 | 10/2018 |
| WO | 2019004854 | A1 | 1/2019 |
| WO | 2019083104 | A1 | 5/2019 |
| WO | 2020033752 | A1 | 2/2020 |
| WO | 2021154427 | A1 | 8/2021 |
| WO | 2021158332 | A1 | 8/2021 |
| WO | 2022108589 | A1 | 5/2022 |
| WO | 2022/159333 | A1 | 7/2022 |
| WO | 2022/251425 | A1 | 12/2022 |
| WO | 2023086394 | A1 | 5/2023 |
| WO | 2024118072 | A1 | 6/2024 |
| WO | 2024151250 | A1 | 7/2024 |
| WO | 2024162961 | A1 | 8/2024 |

OTHER PUBLICATIONS

U.S. Appl. No. 17/556,942, filed Dec. 20, 2021 Advisory Action dated Sep. 1, 2023.

U.S. Appl. No. 17/556,942, filed Dec. 20, 2021 Final Office Action dated Jul. 12, 2023.

U.S. Appl. No. 17/561,458, filed Dec. 23, 2021 Final Office Action dated Sep. 12, 2023.

U.S. Appl. No. 17/561,504, filed Dec. 23, 2021 Final Office Action dated Jul. 19, 2023.

U.S. Appl. No. 17/863,898, filed Jul. 13, 2022 Non-Final Office Action dated Jul. 17, 2023.

U.S. Appl. No. 17/902,705, filed Sep. 2, 2022 Final Office Action dated Aug. 17, 2023.

PCT/US2022/049418 filed Nov. 9, 2022 International Search Report and Written Opinion dated Feb. 10, 2023.

U.S. Appl. No. 17/526,994, filed Nov. 15, 2021 Restriction Requirement dated Jan. 3, 2023.

U.S. Appl. No. 17/556,942, filed Dec. 20, 2021 Non-Final Office Action dated Jan. 31, 2023.

U.S. Appl. No. 17/561,504, filed Dec. 23, 2021 Non-Final Office Action dated Mar. 14, 2023.

PCT/US2020/066707 filed Dec. 22, 2020 International Search Report and Written Opinion dated Apr. 15, 2021.

PCT/US2022/012373 filed Jan. 13, 2022 International Search Report and Written Opinion dated Apr. 19, 2022.

U.S. Appl. No. 17/373,568, filed Jul. 12, 2021 Non-Final Office Action dated Nov. 9, 2023.

U.S. Appl. No. 17/526,994, filed Nov. 15, 2021 Advisory Action dated Jan. 19, 2024.

U.S. Appl. No. 17/526,994, filed Nov. 15, 2021 Final Office Action dated Oct. 24, 2023.

U.S. Appl. No. 17/532,454, filed Nov. 22, 2021 Final Office Action dated Sep. 27, 2023.

U.S. Appl. No. 17/532,454, filed Nov. 22, 2021 Notice of Allowance dated Dec. 8, 2023.

U.S. Appl. No. 17/542,060, filed Dec. 3, 2021 Non-Final Office Action dated Nov. 28, 2023.

U.S. Appl. No. 17/556,942, filed Dec. 20, 2021 Non-Final Office Action dated Nov. 3, 2023.

U.S. Appl. No. 17/561,458, filed Dec. 23, 2021 Notice of Allowance dated Dec. 6, 2023.

U.S. Appl. No. 17/561,504, filed Dec. 23, 2021 Non-Final Office Action dated Nov. 27, 2023.

U.S. Appl. No. 17/561,504, filed Dec. 23, 2021 Notice of Allowance dated Jan. 22, 2024.

U.S. Appl. No. 17/863,898, filed Jul. 13, 2022 Advisory Action dated Jan. 30, 2024.

U.S. Appl. No. 17/863,898, filed Jul. 13, 2022 Final Office Action dated Nov. 22, 2023.

U.S. Appl. No. 17/902,705, filed Sep. 2, 2022 Advisory Action dated Oct. 19, 2023.

U.S. Appl. No. 17/902,705, filed Sep. 2, 2022 Non-Final Office Action dated Dec. 7, 2023.

U.S. Appl. No. 17/526,994, filed Nov. 15, 2021 Final Office Action dated Nov. 19, 2024.

U.S. Appl. No. 17/526,994, filed Nov. 15, 2021 Notice of Allowance dated Feb. 5, 2025.

U.S. Appl. No. 17/571,254, filed Jan. 7, 2022 Non-Final Office Action dated Feb. 13, 2025.

U.S. Appl. No. 17/571,254, filed Jan. 7, 2022 Restriction Requirement dated Oct. 4, 2024.

U.S. Appl. No. 17/863,898, filed Jul. 13, 2022 Advisory Action dated Oct. 28, 2024.

U.S. Appl. No. 17/863,898, filed Jul. 13, 2022 Final Office Action dated Aug. 22, 2024.

U.S. Appl. No. 17/863,898, filed Jul. 13, 2022 Non-Final Office Action dated Dec. 2, 2024.

U.S. Appl. No. 17/902,705, filed Sep. 2, 2022 Advisory Action dated Aug. 1, 2024.

U.S. Appl. No. 17/902,705, filed Sep. 2, 2022 Notice of Allowance dated Sep. 18, 2024.

U.S. Appl. No. 18/274,157, filed Jul. 25, 2023 Non-Final Office Action dated Jan. 17, 2025.

U.S. Appl. No. 18/674,694, filed May 24, 2024 Non-Final Office Action dated Mar. 3, 2025.

U.S. Appl. No. 17/526,994, filed Nov. 15, 2021 Non-Final Office Action dated May 10, 2023.

U.S. Appl. No. 17/532,454, filed Nov. 22, 2021 Non-Final Office Action dated Mar. 22, 2023.

U.S. Appl. No. 17/561,458, filed Dec. 23, 2021 Non-Final Office Action dated Jun. 16, 2023.

(56) References Cited

OTHER PUBLICATIONS

U.S. Appl. No. 17/902,705, filed Sep. 2, 2022 Non-Final Office Action dated May 24, 2023.
U.S. Appl. No. 17/373,568, filed Jul. 12, 2021 Notice of Allowance dated Apr. 26, 2024.
U.S. Appl. No. 17/526,994, filed Nov. 15, 2021 Non-Final Office Action dated Apr. 22, 2024.
U.S. Appl. No. 17/542,060, filed Dec. 3, 2021 Notice of Allowance dated Jun. 3, 2024.
U.S. Appl. No. 17/556,942, filed Dec. 20, 2021 Final Office Action dated Apr. 4, 2024.
U.S. Appl. No. 17/556,942, filed Dec. 20, 2021 Notice of Allowance dated Jun. 26, 2024.
U.S. Appl. No. 17/796,604, filed Jul. 29, 2022 Notice of Allowance dated May 1, 2024.
U.S. Appl. No. 17/863,898, filed Jul. 13, 2022 Non-Final Office Action dated Mar. 11, 2024.
U.S. Appl. No. 17/902,705, filed Sep. 2, 2022 Final Office Action dated May 22, 2024.
PCT/US2022/051431 filed Nov. 30, 2022 International Search Report and Written Opinion dated May 22, 2022.
PCT/US2023/010515 filed Jan. 10, 2023 International Search Report and Written Opinion dated Sep. 12, 2023.
PCT/US2023/012095 filed Feb. 1, 2023 International Preliminary Report on Patentability dated Jul. 31, 2025.
PCT/US2023/012095 filed Feb. 1, 2023 International Search Report and Written Opinion dated Jul. 17, 2023.
U.S. Appl. No. 17/571,254, filed Jan. 7, 2022 Final Office Action dated Aug. 13, 2025.
U.S. Appl. No. 17/863,898, filed Jul. 13, 2022 Advisory Action dated Aug. 6, 2025.
U.S. Appl. No. 17/863,898, filed Jul. 13, 2022 Final Office Action dated Jun. 3, 2025.
U.S. Appl. No. 18/274,157, filed Jul. 25, 2023 Advisory Action dated Jul. 16, 2025.
U.S. Appl. No. 18/274,157, filed Jul. 25, 2023 Final Office Action dated May 5, 2025.
U.S. Appl. No. 18/674,694, filed May 24, 2024 Notice of Allowance dated Jun. 23, 2025.
U.S. Appl. No. 17/873,923, filed Jul. 26, 2022 Non-Final Office Action dated Jan. 27, 2026.
U.S. Appl. No. 18/274,157, filed Jul. 25, 2023 Final Office Action dated Jan. 6, 2026.
U.S. Appl. No. 18/706,737, filed May 1, 2024 Non-Final Office Action dated Mar. 13, 2026.
U.S. Appl. No. 18/882,228, filed Sep. 11, 2024 Notice of Allowance dated Feb. 5, 2026.
EP 25167903.1 filed Apr. 2, 2025 Extended European Search Report dated Oct. 7, 2025.
U.S. Appl. No. 17/863,898, filed Jul. 13, 2022 Notice of Allowance dated Sep. 16, 2025.
U.S. Appl. No. 18/274,157, filed Jul. 25, 2023 Non-Final Office Action dated Sep. 19, 2025.
U.S. Appl. No. 18/622,604, filed Mar. 29, 2024 Non-Final Office Action dated Oct. 2, 2025.
U.S. Appl. No. 18/882,228, filed Sep. 11, 2024 Non-Final Office Action dated Oct. 1, 2025.
U.S. Appl. No. 18/899,727, filed Sep. 27, 2024 Notice of Allowance dated Sep. 30, 2025.
U.S. Appl. No. 17/571,254, filed Jan. 7, 2022 Non-Final Office Action dated Mar. 25, 2026.
U.S. Appl. No. 18/274,157 filed Jul. 25, 2023 Notice of Allowance dated Mar. 30, 2026.
U.S. Appl. No. 18/622,604, filed Mar. 29, 2024 Final Office Action dated Apr. 7, 2026.
U.S. Appl. No. 18/899,727, filed Sep. 27, 2024 Notice of Allowance dated Mar. 19, 2026.

* cited by examiner

FIG. 2C
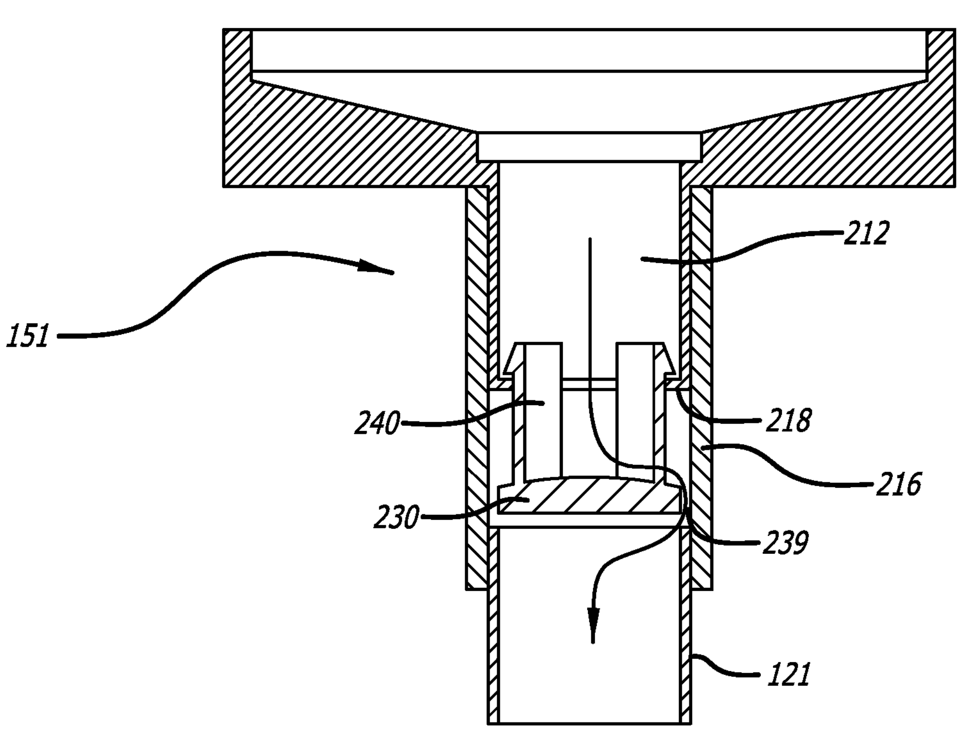
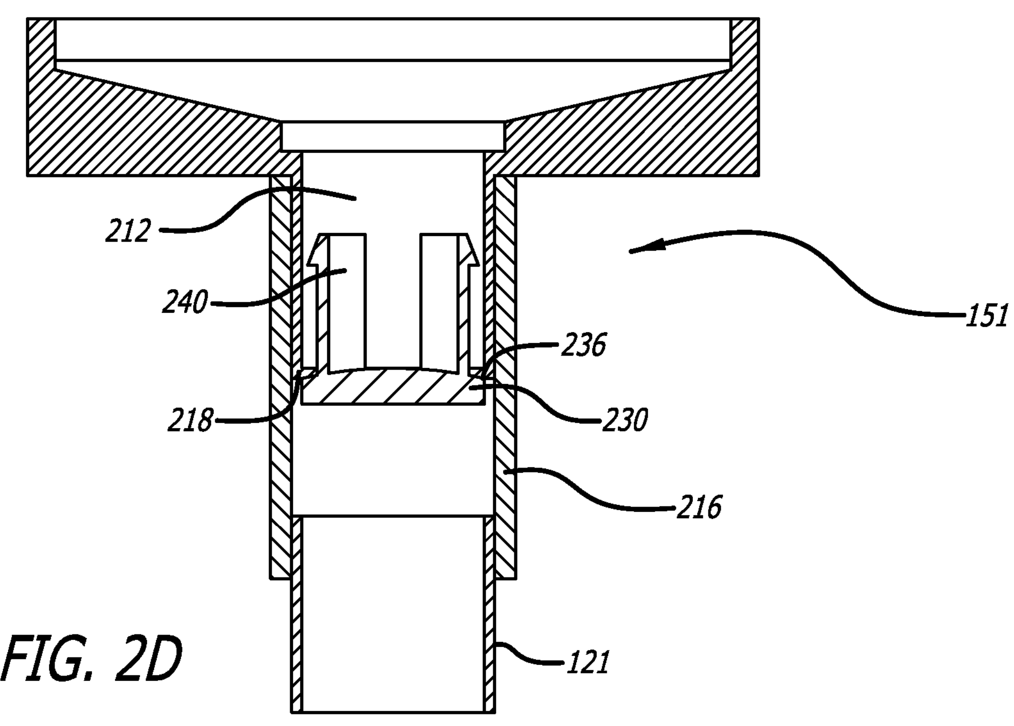
FIG. 2D

VACUUM CHAMBER WITH SNAP FIT PLUNGER MECHANISM

PRIORITY

This application claims the benefit of priority to U.S. Provisional Application No. 63/164,951, filed Mar. 23, 2021, which is incorporated by reference in its entirety into this application.

BACKGROUND

The draining of liquid (e.g., urine) from a patient may include the use of a liquid drainage system including a flexible drainage tube extending from a drainage catheter to a collection container. Typical catheters include indwelling catheters, Foley catheters, balloon catheters, peritoneal drainage catheters, or the like, and are configured to be inserted into an orifice within the body of a patient to drain a liquid therefrom. In some instances, the flexibility of the drainage tube can form sections of positive incline, also termed "dependent loops," along the drainage tube where drainage liquid can accumulate. Liquid pooling within dependent loops can cause various complications. For example, urine pooling can be a source of catheter associated urinary tract infection ("CAUTI") causing agents such as bacteria, microbes, and the like. Hospital Acquired Infections ("HAI"), such as CAUTI, are detrimental to the patient, and also incur extra costs in treating these additional complications. Embodiments disclosed herein are directed to clearing drainage liquid from dependent loops thereby, reducing patient risk.

SUMMARY

Briefly summarized, disclosed herein is a drainage system for draining a liquid from a patient. The system includes a drainage tube configured to receive drainage liquid from the patient. A distal end of the drainage tube is configured to couple with a drainage catheter. The system further includes a vacuum chamber configured to receive the drainage liquid from the drainage tube. The chamber includes an input port coupled with the drainage tube at a proximal end of the drainage tube and a drain port coupled with an output tube, where the output tube is configured for transporting the drainage liquid from the vacuum chamber to a collection container. The system also includes an air pump having an input coupled with a vacuum port of the vacuum chamber and an output coupled with the drainage tube at a junction point adjacent the distal end of the drainage tube. Activation of the air pump establishes circulating fluid flow between the drainage tube and the vacuum chamber, and deactivation of the air pump allows drainage liquid to drain from the vacuum chamber into the output tube.

The system may further include a drain valve in line with the drain port, where the drain valve is configured to transition between an open state and a closed state, such that in the open state, fluid flow through the drain port is allowed, and in the closed state, fluid flow through the drain port is prevented. The drain valve may include a plunger displaceable between a "down" position when the drain valve is in the open state, and an "up" position when the drain valve is in the closed state. The plunger may include a plurality of posts coupled with and extending vertically away from a circular base, where the posts are coupled with the drainage port via a snap fit coupling, and the snap fit coupling is configured to limit downward displacement of the plunger to define the "down" position.

The base may include an annular sealing ledge extending along a circumference of the base, and the annular sealing ledge is configured to form a seal with a corresponding annular sealing edge of the drain port when the plunger is disposed in the "up" position, to define the closed state of the drain valve. Activation of the air pump may define a vacuum within the vacuum chamber, and the vacuum exerts an upward force on the plunger to displace the plunger to the "up" position. Conversely, deactivation of the air pump relieves the vacuum within the vacuum chamber, allowing the plunger to self-displace to the "down" position.

A bottom wall of the chamber may be sloped toward the drain port to facilitate complete drainage of liquid from the vacuum chamber. In use, drainage liquid may flow perpendicularly onto the base of the plunger, and radially outward between the posts. The top side of the base may include a radially outward sloped surface to prevent accumulation of drainage liquid on the top side.

The system may include an isolation valve disposed in line with the drainage tube at a location distal the junction point and the isolation valve may be configured to prevent fluid flow toward the catheter. The isolation valve may be configured to transition between a closed state and open state in accordance with activation and deactivation of the air pump, respectively. The isolation valve may be a check valve configured to allow proximal fluid flow through the isolation valve and prevent distal fluid flow through the isolation valve. The system may include a connector disposed at the distal end of the drainage tube, and the junction point and the isolation valve may be integral to the connector.

Also disclosed herein is a method of draining liquid from a patient. The method includes providing a drainage system including a drainage pathway having a distal end and a proximal end, and coupling the distal end of the drainage pathway with a catheter, where the catheter is in fluid communication with a drainage liquid source within a patient. The method further includes establishing a passive flow of drainage liquid from the patient to the drainage pathway. Additional method steps include accumulating a volume of the drainage liquid at a first location along the drainage pathway, moving the liquid volume from the first location to a second location along the drainage pathway, accumulating the liquid volume at the second location, and moving the liquid volume from the second location to a collection container.

In some embodiments of the method, the drainage pathway includes a drainage tube coupled with the catheter, and the first location is between a distal end and a proximal end of the drainage tube. Moving the liquid volume from the first location to the second location may include establishing a pressure difference across the liquid volume and moving the liquid volume from the second location to the collection container may include opening a drain valve. Accumulating the liquid volume at the second location may include closing the drain valve and establishing the pressure difference across the liquid volume may cause the drain valve to close. Conversely, removing the pressure difference across the liquid volume may allow the drain valve to open.

Also disclosed herein is a system for moving drainage liquid proximally along a drainage tube from a drainage catheter to a collection container. This system includes a vacuum chamber. The vacuum chamber includes an input port coupleable with the drainage tube at the proximal end and a drain port having output tube, where the output tube is coupleable with a collection container. This system further includes an air pump having an input, coupled with a vacuum port of the vacuum chamber, and a three-way connector. The three-way connector includes a first port coupleable with the catheter, a second port coupleable with the distal end of the drainage tube, and a third port coupled with an output of the air pump, where the first, second, and third ports are in fluid communication with each other. In use, activation of the air pump establishes circulating fluid flow between the drainage tube and the vacuum chamber to move drainage liquid proximally along the drainage tube to the vacuum chamber, and deactivation of the air pump allows drainage liquid to drain from the vacuum chamber into the collection container.

This system may also include a drain valve in line with the drain port, and the drain valve is configured to transition between an open state and a closed state. In the open state, fluid flow through the drain port is allowed, and in the closed state, fluid flow through the drain port is prevented. The drain valve may include a plunger displaceable between a "down" position when the drain valve is in the open state, and an "up" position when the drain valve is in the closed state. The plunger may include a plurality of posts coupled with and extending vertically away from a circular base. The posts may be coupled with the drainage port via a snap fit coupling, and the snap fit coupling may be configured to limit downward displacement of the plunger to define the "down" position. The base may include an annular sealing ledge extending along a circumference of the base, where the annular sealing ledge is configured to form a seal with a corresponding annular sealing edge of the drain port when the plunger is disposed in the "up" position, and the seal may define the closed state of the drain valve.

Activation of the air pump may define a vacuum within the vacuum chamber, and the vacuum may exert an upward force on the plunger to displace the plunger to the "up" position. Conversely, deactivation of the air pump may remove the vacuum within the vacuum chamber, allowing the plunger to self-displace to the "down" position.

A bottom wall of the vacuum chamber may be sloped toward the drain port to facilitate complete drainage of liquid from the vacuum chamber. In use, the drainage liquid may flow perpendicularly onto the base and radially outward between the posts. The top side of the base may include a radially outward sloped surface to prevent accumulation of drainage liquid on the top side.

This system may further include an isolation valve disposed in line with the first port of the connector where the isolation valve is configured to prevent fluid flow toward the catheter. The isolation valve may be configured to transition between a closed state and an open state in accordance with activation and deactivation of the air pump, respectively. The isolation valve may be a check valve configured to allow proximal fluid flow through the first port and prevent distal fluid flow through the first port.

These and other features of the concepts provided herein will become more apparent to those of skill in the art in view of the accompanying drawings and the following description, which describe particular embodiments of such concepts in greater detail.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 2C is a detail cross-sectional illustration of the plunger valve of FIG. 2A with the plunger disposed in the "down" position, in accordance with some embodiments disclosed herein.

FIG. 2D is a detail cross-sectional illustration of the plunger valve of FIG. 2A with the plunger disposed in the "up" position, in accordance with some embodiments disclosed herein.

DETAILED DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The phrases "connected to" and "coupled with" refer to any form of interaction between two or more entities, including mechanical, electrical, magnetic, electromagnetic, fluid, and thermal interaction. Two components may be connected or coupled with each other even though they are not in direct contact with each other. For example, two components may be coupled with each other through an intermediate component.

The directional terms "proximal" and "distal" are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user. The term “fluid” is used herein to refer to either a gas or a liquid.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Figure 1:
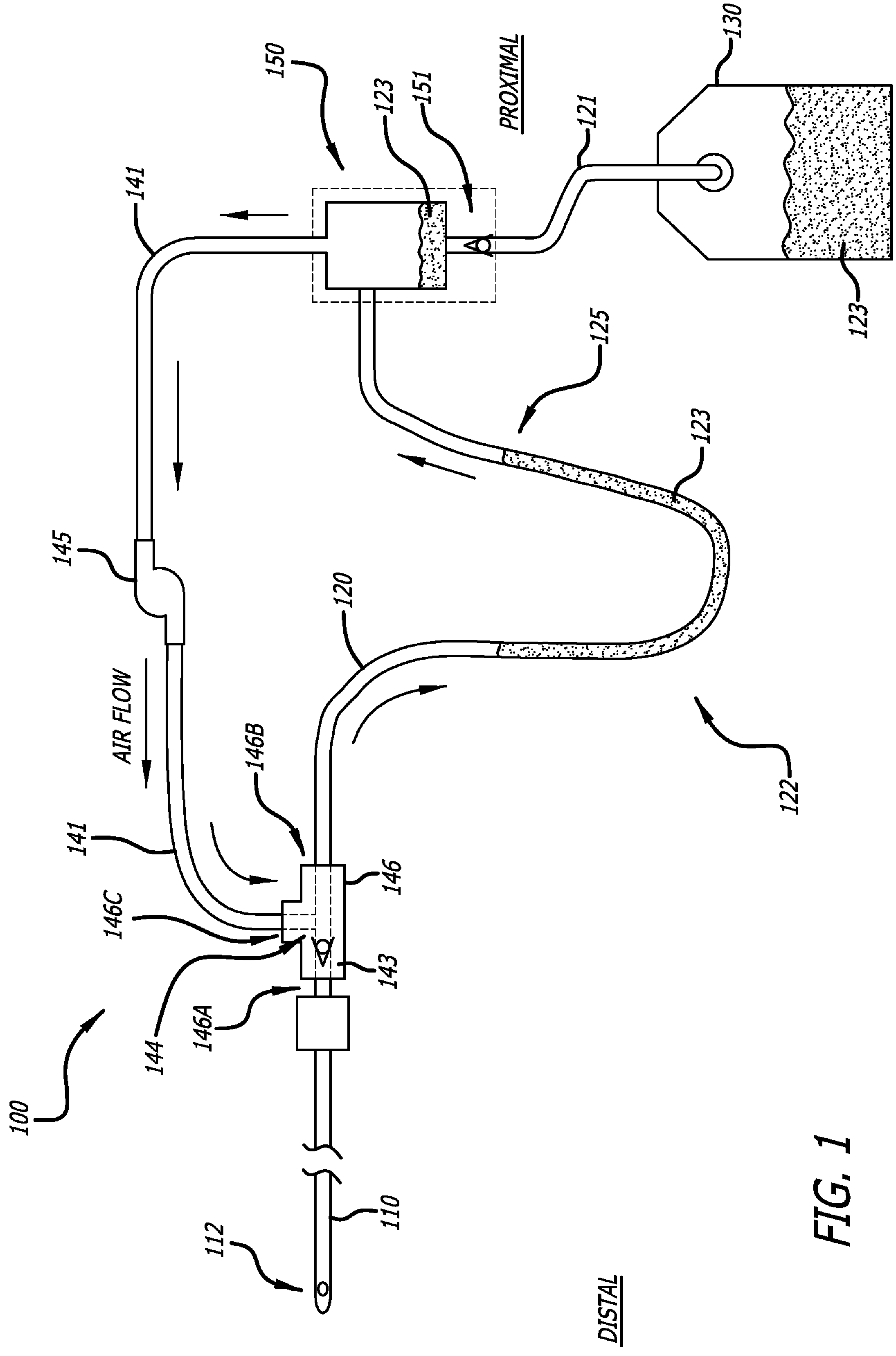
FIG. 1 shows an exemplary catheter and a liquid collection system including a vacuum chamber assembly, in accordance with some embodiments disclosed herein.

FIG. 1 shows an exemplary drainage system (“system”) 100, including a catheter 110, a drainage tube 120, a collection container 130, and a vacuum chamber assembly 150. The catheter 110 includes an eyelet 112 that provides fluid communication with a lumen of the catheter 110, and is configured to drain a liquid 123 from liquid source within a patient. In general, the system provides a drainage pathway to transport liquid 123 from the catheter 110 to the collection container 130

The drainage tube 120 extends from the catheter 110 to the vacuum chamber 150. A collection tube 121 extends from the vacuum chamber assembly 150 to the collection container 130. In use, liquid 123 from the patient may flow from the catheter 110, through the drainage tube 120, and into the vacuum chamber assembly 150. The liquid 123 may then flow out of the vacuum chamber assembly 150, through the collection tube 121, and into the collection container 130. The drainage tube 120 and the collection tube 121 can be formed of rubber, plastic, polymer, silicone, or similar suitable material. The collection container 130 can include a rigid container, a flexible collection bag, or similar suitable container for receiving a liquid, e.g., urine, drained from the catheter 110. In operation, the drainage system 100 may facilitate a passive draining process of liquid 123 from the patient without incident. In some instances, one or more complications may arise during the passive draining process requiring corrective action.

As shown in FIG. 1, the flexibility of the drainage tube 120 can result in sections of the drainage tube 120 having one or more dependent loops 122 followed by a positive incline section 125. The positive incline section 125 can lead to liquid pooling (i.e., accumulation) within the dependent loop 122 of the drainage tube 120. A dependent loop 122 may be any portion of the drainage tube 120 that is lower than a downstream portion so as to create a positive incline 125 relative to the direction of fluid flow. Dependent loops 122 can form in slack portions of the drainage tube 120. The dependent loop 122 may be a complete loop, a partial loop, or any segment of tubing 120 that causes liquid 123 to pool in the drainage tube 120.

In instances of pooling, a drainage tube clearing process, as described herein, may provide a corrective action to the pooling of liquid 123. In the illustrated embodiment, an air pump 145 can provide a pressure difference across a volume of pooled liquid 123 within the drainage tube 120 to proximally move the pooled liquid 123 along the drainage tube 120. Air tubing 141 fluidly couples an input of the air pump 145 to the vacuum chamber assembly 150 and further couples an output of the air pump 145 to the drainage tube 120 at a junction point 144 adjacent the catheter 110.

In some embodiments, the system 100 may include a three-way connector 146 disposed between the catheter 110 and the drainage tube 120 and the connector 146 includes a fluid flow path from the catheter 110 to the drainage tube 120. The catheter 110 may be coupled with the connector 146 at a first or proximal port 146A and the distal end of the drainage tube 120 may be coupled with a second or distal port 146B. The air tubing 141 may be coupled with a third or side port 146C of the connector 146 so that the catheter 110, the drainage tube 120 and the air tubing 141 are fluid communication with each other. As such, the junction point 144 may be integral to the connector 146.

During air pump operation, the air pump 145 pulls air from the vacuum chamber assembly 150 and delivers the air to the drainage tube 120 at the junction point 144 to define an air pressure difference across the pooled liquid 123 disposed in the dependent loop 122. As a result, the pressure difference moves the liquid 123 proximally up the positive incline 125, along the drainage tube 120, and into the vacuum chamber assembly 150.

In some instances, during operation of the air pump 145, a vacuum may be generated within the vacuum chamber assembly 150. In such an instance, if left unimpeded, air or liquid 123 may be drawn from the collection container 130, through the collection tube 121, and into the vacuum chamber assembly 150. To prevent reverse flow in the collection tube 121, the vacuum chamber assembly 150 includes plunger valve 151 to define a check-valve function in line with the drain port 212.

In use, in the event of pooling liquid 123 within the drainage tube, the air pump 145 may be activated. When the air pump 145 is activated, air is pulled from the vacuum chamber assembly 150 and delivered to the drainage tube 120 at the junction point 144, i.e., upstream of the pooled liquid 123. The plunger valve 151 closes to prevent reverse flow in the collection tube 121. The pooled liquid 123 is moved into the vacuum chamber assembly 150 accumulating therein. Thereafter, the air pump 145 is deactivated which relieves the vacuum within the vacuum chamber assembly 150. As a result, the plunger valve 151 opens and the accumulated liquid 123 within the vacuum chamber assembly 150 drains into the collection container 130.

In the illustrated embodiment, the vacuum chamber assembly 150 is disposed above the collection container 130 so that the liquid 123 may passively flow from the vacuum chamber assembly 150 to the collection container 130. In some embodiments, the collection tube 121 is routed so as to prevent pooling of liquid 123 within the collection tube 121 between the chamber assembly 150 and the collection container 130. In some embodiments, the vacuum chamber assembly 150 may be located in close proximity to the collection container so that the collection tube 121 may be relatively short, such as about 1 to 2 feet in length, for example.

In an embodiment, the system 100 may include a safety or isolation valve 143 disposed between the catheter 110 and the drainage tube 120. More specifically, the safety valve 143 may be disposed between the catheter 110 and the junction point 144. The safety valve 143 may at least partially isolate the catheter 110 from the drainage tube 120. In other words, the safety valve 143, when closed, may prevent an internal pressure of the drainage tube 120 from affecting a pressure within the catheter 110. Similarly, the safety valve 143, when closed, may prevent liquid 123 within the drainage tube 120 from flowing into the catheter 110. The safety valve 143 can transition between a closed position and an open position. In the illustrated embodiment, the safety valve 143 is a check valve configured to prevent fluid flow toward the catheter 110. As such, the safety valve 143 may prevent a positive pressure, as may be present within the drainage tube 120, from reaching the patient. In some embodiments, the safety valve 143 may be integral to the connector 146.

In other embodiments, the safety valve 143 may be a manually operated valve, such as a tubing clamp or a pinch valve. In still other embodiments, the safety valve 143 may be an electro-mechanical valve, e.g., a solenoid valve or the like. In such an embodiment, the safety valve 143 may be coupled with the air pump 145 so that the safety valve 143 is actuated toward the closed position when the air pump 145 is actuated.

Figure 2A:
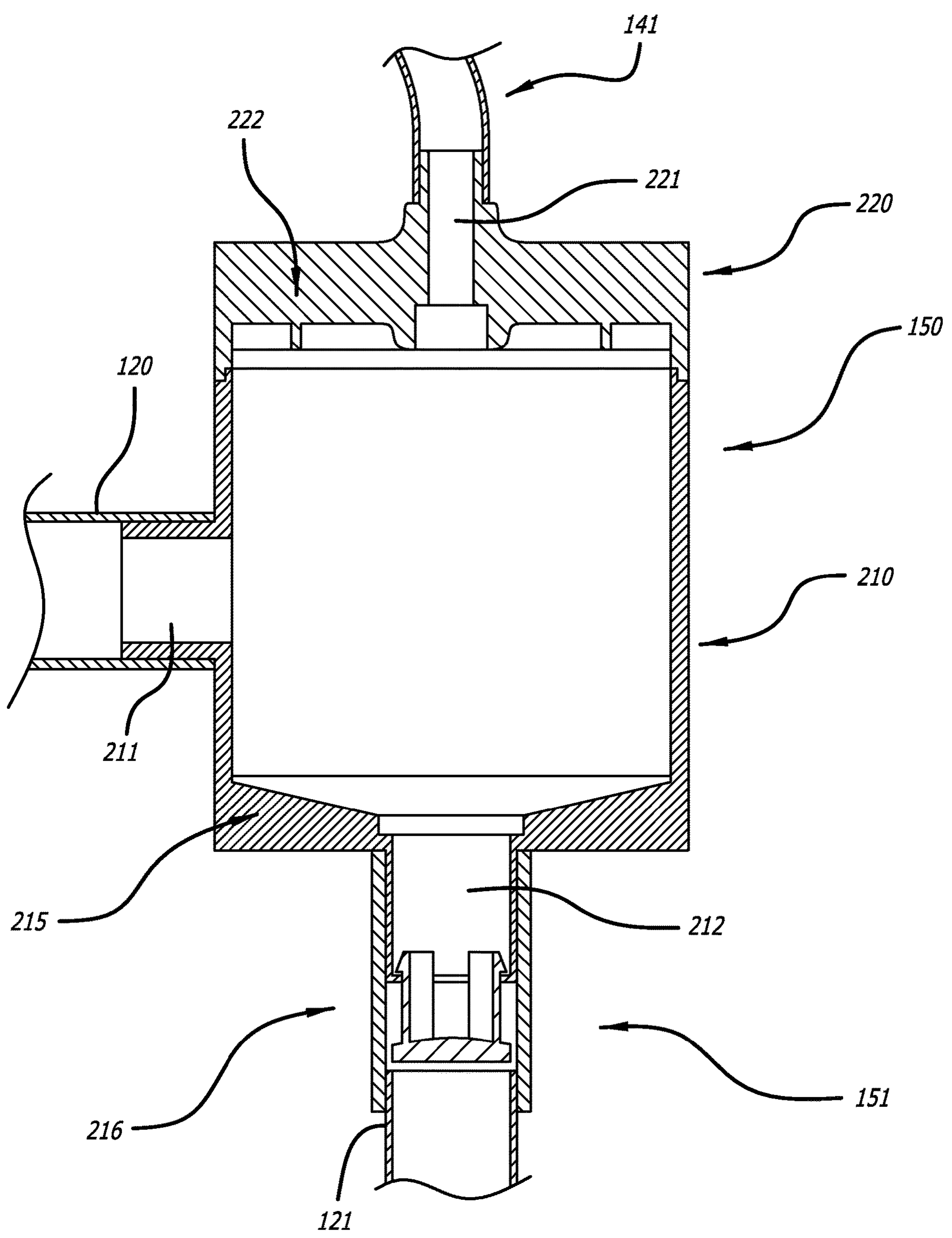
FIG. 2A is a cross-sectional illustration of the vacuum chamber assembly of FIG. 1, in accordance with some embodiments disclosed herein.

FIGS. 2A-2D illustrate various views of the vacuum chamber assembly 150. FIG. 2A is a cross-sectional front view of the vacuum chamber assembly 150 illustrating various components and features. The vacuum chamber assembly 150 includes a chamber housing 210 having an inlet port 211 and a drain port 212. The drainage tube 120 is coupled with the inlet port 211 and the collection tube 121 is coupled with the drain port 212 via a coupling adapter 216. A bottom wall of the housing 210 includes a sloped surface 215 to facilitate complete drainage of liquid 123 from the housing 210. An internal volume of the vacuum chamber assembly 150 may be greater than an internal volume of the drainage tube 120.

The housing 210 is closed on the top by a cap 220 having vacuum port 221 and the air tubing 141 is coupled with the vacuum port 221. Both the housing 210 and the cap 220 may be formed of plastic material via the injection molding process. Each of the housing 210 and the cap 220 may include strengthening rips such as the ribs 222. The cap 220 may be sealably attached to the housing 210 via any suitable joining process for the plastic material, such as ultra-sonic welding, solvent bonding, adhesive bonding, and the like.

Figure 2B:
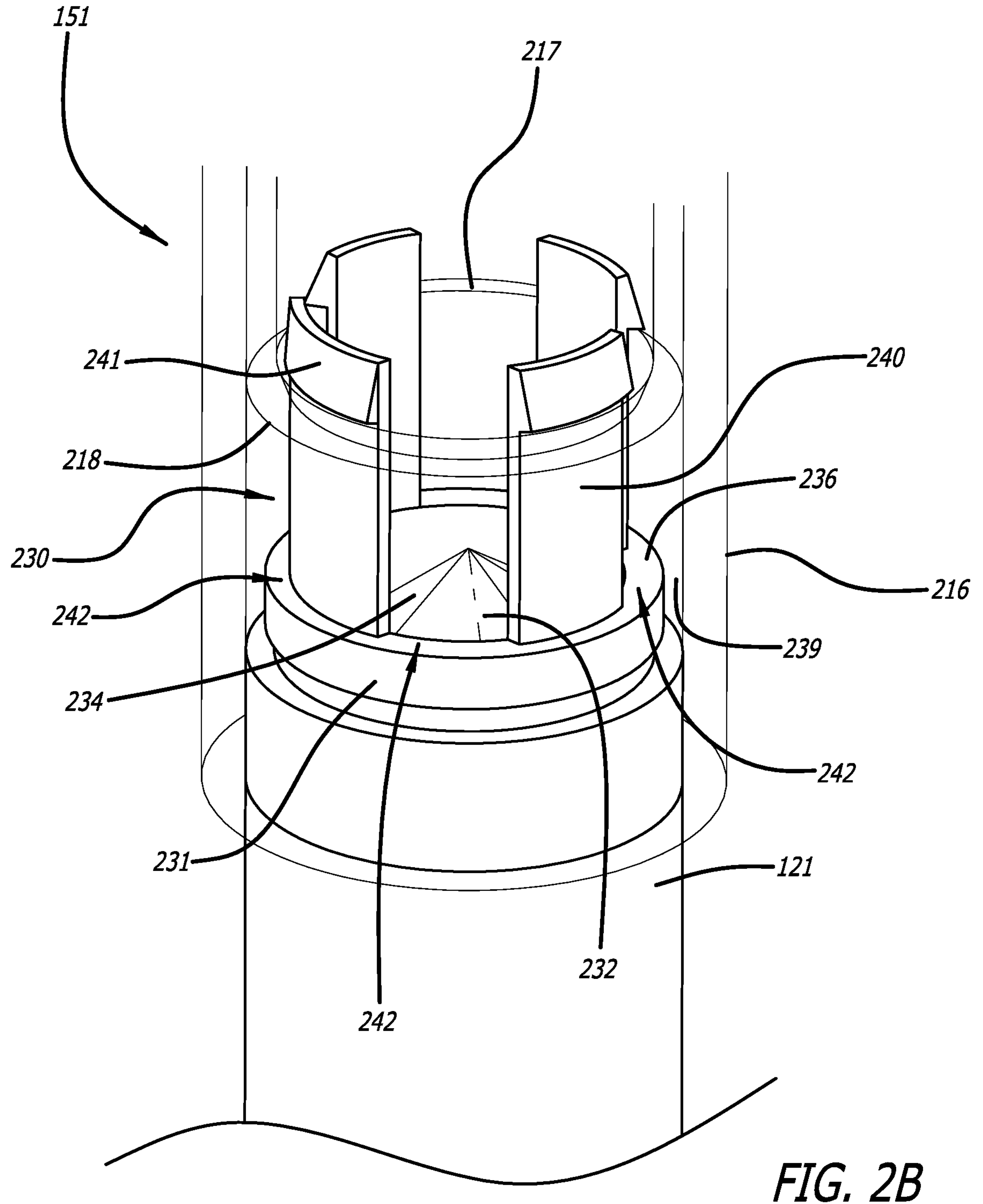
FIG. 2B is a perspective detail illustration of the plunger of FIG. 2A, in accordance with some embodiments disclosed herein.

FIGS. 2B-2D illustrate components, features, and functionality of the plunger valve 151. FIG. 2B illustrates a detail perspective view of the plunger valve 151 and related components. FIG. 2C shows the plunger in a “down” or open position, and FIG. 2D shows the plunger 230 in an “up” or closed position. The plunger valve 151 includes a displaceable plunger 230 having a circular base 231. A top side 232 of the base 231 includes a radially outward sloped surface 234 to prevent accumulation of the liquid 123 on the top side 231 as it drains from the housing 210.

In the illustrated embodiment, four deflectable posts 240 are coupled with and extend away from the top side 232 and each post 240 includes a hook 241 at a free end. In other embodiments, the plunger 230 may include 2, 3, 5, or more posts 240. The drain port 212 includes an inward protruding annular hook ledge 217 configured to engage the hooks 241 in a snap fit relationship. The engagement of the hooks 241 with the hook ledge 217 limits the downward displacement of the plunger 230 at the “down” position as shown in FIG. 2C. The spaces 242 between the posts 244 define a flow path for the liquid 123 as it drains from the housing 210. A diameter of the base 231 is less than an inside diameter of the coupling adapter 216 to define an annular flow path 239 for the liquid 123 as it flows downward past the base 231 as illustrated in FIG. 2C.

The plunger 230 further includes an annular sealing ledge 236 disposed on the top side 231 and the drain port 212 includes a corresponding annular sealing edge 218 at the bottom end of the drain port 212. The annular sealing ledge 236 and the corresponding annular sealing edge 218 are configured to the define a seal between the plunger 230 and the drain port 212 when the plunger 230 is disposed in the “up” position as show in FIG. 2D.

In use, with the plunger 230 in the “down” position, the liquid 123 drains from the housing 210, through the drain port 212, and flows perpendicularly onto the top side 231 of the plunger 230 where it flows radially outward along the sloped surface 234 and through the spaces 242 between the posts 240. The liquid 123 then flows downward through the annular flow path 239 and into the collection tube 121. In further use, when the air pump 145 is activated, vacuum within the housing 210 draws the plunger 230 to the “up” position, so that the annular sealing ledge 236 engages the corresponding annular sealing edge 218 to seal off the drain port 212, thereby preventing air and/or liquid 123 from flowing upward through the drain port 212.

By way of summary, use of the system 100 may include one or more of the following steps or processes. The system 100 may be set up by coupling the distal end of the drainage tube 120 with the catheter 110 and routing the drainage tube 120 toward the collection container 130. The vacuum chamber assembly 150 may be located below the patient to facilitate passive flow of liquid 123 from the patient to the vacuum chamber assembly 150, and the vacuum chamber assembly 150 may be located above the collection container 130 to facilitate passive flow of liquid 123 from the vacuum chamber assembly 150 to the collection container 130. The output tube 121 may be coupled with the collection container 130. As liquid 123 flows from the catheter 110 into the drainage tube 120, a volume of liquid 123 may accumulate within a dependent loop 122 of the drainage tube 120. In response to the accumulated volume of liquid 123 in the drainage tube 120, the air pump 145 may be activated causing a vacuum within the vacuum chamber assembly 150 and/or a positive pressure within the drainage tube distal the dependent loop 122 which establishes an air pressure difference across the accumulated volume of liquid 123. The air pressure difference moves the accumulated volume of liquid 123 proximally along the drainage tube 120 and into the vacuum chamber assembly 150. The vacuum within the vacuum chamber assembly 150 causes the plunger 130 to displace to the “up” position to seal off the drain port 212, so that the volume of liquid 123 may accumulate in the vacuum chamber assembly 150. In response to the accumulated volume of liquid 123 in the vacuum chamber assembly 150, the air pump 145 may be deactivated, relieving the vacuum within the vacuum chamber assembly 150, which allows the plunger 130 to fall to the “down” position. The accumulated volume of liquid 123 in the vacuum chamber assembly 150 may then drain from the vacuum chamber assembly 150 into the collection container 130.

In some instances, liquid 123 may flow from the catheter 110, through the drainage tube 120, through the vacuum chamber assembly 150, and into the collection container 130 with accumulating a volume liquid 123 along the drainage tube 120 or within the vacuum chamber assembly 150.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A drainage system for draining a liquid from a patient, the drainage system comprising:

a drainage tube configured to receive drainage liquid from the patient, a distal end of the drainage tube configured to couple with a catheter;

a vacuum chamber configured to receive the drainage liquid from the drainage tube, the vacuum chamber comprising:

an input port coupled with the drainage tube at a proximal end of the drainage tube; and a drain port coupled with an output tube, the output tube configured for transporting the drainage liquid from the vacuum chamber to a collection container;

a drain valve in line with the drain port, the drain valve configured to transition between an open state in which fluid flow through the output tube is permitted and a closed state in which fluid flow through the output tube is prevented, wherein the drain valve comprises a plunger displaceable between a "down" position in accordance with the drain valve disposed in the open state, and an "up" position in accordance with the drain valve disposed in the closed state; and an air pump having an input coupled with a vacuum port of the vacuum chamber and an output coupled with the drainage tube at a junction point adjacent the distal end, wherein:

upon activation of the air pump, circulating fluid flow is established between the drainage tube and the vacuum chamber, upon deactivation of the air pump, the drainage liquid drains from the vacuum chamber into the collection container, and the drainage liquid is prevented from draining into the collection container only when the air pump is activated.

2. The system of claim 1, wherein the plunger comprises a plurality of deflectable posts coupled with a circular base, the plurality of deflectable posts extending vertically away from the circular base.

3. The system of claim 2, wherein the plurality of deflectable posts are coupled with the drain port via a snap fit coupling, the snap fit coupling configured to limit downward displacement of the plunger, defining the "down" position.

4. The system of claim 2, wherein the circular base comprises an annular sealing ledge extending along a circumference of the circular base, the annular sealing ledge configured to form a seal with a corresponding annular sealing edge of the drain port when the plunger is disposed in the "up" position, and wherein the seal defines the closed state of the drain valve.

5. The system of claim 2, wherein in use, the drainage liquid flows perpendicularly onto the circular base of the plunger, and radially outward between the plurality of deflectable posts.

6. The system of claim 2, wherein a top side of the circular base comprises a radially outward sloped surface to prevent accumulation of the drainage liquid.

7. The system of claim 1, wherein:

activation of the air pump defines a vacuum within the vacuum chamber, the vacuum exerting an upward force on the plunger to displace the plunger to the "up" position, and deactivation of the air pump relieves the vacuum within the vacuum chamber, allowing the plunger to self-displace to the "down" position.

8. The system of claim 1, wherein a bottom wall of the vacuum chamber is sloped toward the drain port to facilitate complete drainage of the drainage liquid from the vacuum chamber.

9. The system of claim 1, further comprising an isolation valve disposed in line with the drainage tube at a location distal the junction point, the isolation valve configured to prevent fluid flow toward the catheter.

10. The system of claim 9, wherein the isolation valve is configured to transition between a closed state and open state in accordance with activation and deactivation of the air pump, respectively.

11. The system of claim 9, wherein the isolation valve is a check valve configured to allow proximal fluid flow through the isolation valve and prevent distal fluid flow through the isolation valve.

12. The system of claim 9, further comprising a connector disposed at the distal end of the drainage tube, wherein the junction point and the isolation valve are integral to the connector.

13. A system for moving drainage liquid proximally along a drainage tube from a drainage catheter to a collection container, comprising:

a vacuum chamber comprising:

an input port coupleable with the drainage tube at a proximal end; and a drain port having an output tube, the output tube coupleable with the collection container;

a drain valve in line with the drain port, the drain valve configured to transition between an open state in which fluid flow through the output tube is permitted and a closed state in which fluid flow through the output tube is prevented, wherein the drain valve comprises a plunger displaceable between a "down" position in accordance with the drain valve disposed in the open state, and an "up" position in accordance with the drain valve disposed in the closed state;

an air pump having an input coupled with a vacuum port of the vacuum chamber; and a three-way connector comprising:

a first port couplable with the drainage catheter;

a second port couplable with a distal end of the drainage tube; and a third port coupled with an output of the air pump, the first port, the second port, and the third port in fluid communication with each other, wherein in use:

activation of the air pump establishes a circulating fluid flow between the drainage tube and the vacuum chamber to move the drainage liquid proximally along the drainage tube to the vacuum chamber, deactivation of the air pump allows the drainage liquid to drain from the vacuum chamber into the collection container, and the drainage liquid is prevented from draining into the collection container only when the air pump is activated.

14. The system of claim 13, wherein the plunger comprises a plurality of deflectable posts coupled with a circular base, the plurality of deflectable post extending vertically away from the circular base.

15. The system of claim 14, wherein the plurality of deflectable posts are coupled with the drain port via a snap fit coupling, the snap fit coupling configured to limit downward displacement of the plunger defining the "down" position.

16. The system of claim 14, wherein the circular base comprises an annular sealing ledge extending along a circumference of the circular base, the annular sealing ledge configured to form a seal with a corresponding annular sealing edge of the drain port when the plunger is disposed in the “up” position, and wherein the seal defines the closed state of the drain valve.

17. The system of claim 14, wherein in use, the drainage liquid flows onto the circular base and radially outward between the plurality of deflectable posts.

18. The system of claim 14, a top side of the circular base comprises a radially outward sloped surface to prevent accumulation of the drainage liquid.

19. The system of claim 13, wherein:

activation of the air pump defines a vacuum within the vacuum chamber, the vacuum exerting an upward force on the plunger to displace the plunger to the “up” position, and deactivation of the air pump relieves the vacuum within the vacuum chamber, allowing the plunger to self-displace to the “down” position.

20. The system of claim 13, wherein a bottom wall of the vacuum chamber is sloped toward the drain port to facilitate complete drainage of liquid from the vacuum chamber.

21. The system of claim 13, further comprising an isolation valve disposed in line with the first port of the three-way connector, the isolation valve configured to prevent fluid flow toward the drainage catheter.

22. The system of claim 21, wherein the isolation valve is configured to transition between a closed state and open state in accordance with activation and deactivation of the air pump, respectively.

23. The system of claim 21, wherein the isolation valve is a check valve configured to allow proximal fluid flow through the first port and prevent distal fluid flow through the first port.

* * * * *